US011457888B2

(12) United States Patent
Uebler

(10) Patent No.: US 11,457,888 B2
(45) Date of Patent: Oct. 4, 2022

(54) METHOD FOR GENERATING A KNOWLEDGE BASE USEFUL IN IDENTIFYING AND/OR PREDICTING A MALFUNCTION OF A MEDICAL DEVICE

(71) Applicant: Siemens Healthcare GmbH, Erlangen (DE)

(72) Inventor: Moritz Uebler, Obermichelbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 803 days.

(21) Appl. No.: 16/413,812

(22) Filed: May 16, 2019

(65) Prior Publication Data

US 2019/0357873 A1    Nov. 28, 2019

(30) Foreign Application Priority Data

May 22, 2018 (EP) .................................... 18173511

(51) Int. Cl.
*A61B 6/00* (2006.01)
*G16H 40/40* (2018.01)
(Continued)

(52) U.S. Cl.
CPC ............ *A61B 6/586* (2013.01); *G16H 40/40* (2018.01); *G16H 40/60* (2018.01); *G07C 3/00* (2013.01)

(58) Field of Classification Search
None
See application file for complete search history.

(56) References Cited

U.S. PATENT DOCUMENTS 7,882,394 B2   2/2011 Hosek et al.
2008/0004840 A1*  1/2008 Pattipatti ............ G05B 23/0251
                                                    702/183
(Continued)

FOREIGN PATENT DOCUMENTS

WO    WO 2016026681 A1    2/2016

OTHER PUBLICATIONS

Wang et al., Research on Fault Diagnosis Expert System Based on the Neural Network and the Fault Tree Technology, Procedia Engineering 31 (2012) 1206-1210, doi:10.1016/j.proeng.2012.01.1164 (Year: 2012).*

(Continued)

*Primary Examiner* — Devin C Hein
(74) *Attorney, Agent, or Firm* — Harness, Dickey & Pierce, P.L.C.

(57) ABSTRACT

A method is for generating a knowledge base useful in identifying and/or predicting a malfunction of a medical device. The method includes (a) providing virtual components, each corresponding to a component of the medical device; (b) creating a virtual model of the medical device using the virtual components; (c) rendering at least one virtual output parameter of the virtual model, based upon simulation of a malfunction of at least one of the virtual components; (d) providing the at least one virtual output parameter rendered, to the medical device software; (e) correlating a response of the medical device software to the at least one virtual output parameter rendered; steps (c) to (e) being repeated, based upon a plurality of different simulated malfunctions, and the plurality of different simulated malfunctions and responses of the medical device software correlated being used in the generating of the knowledge base on the medical device.

27 Claims, 3 Drawing Sheets

(51) Int. Cl.
    *G16H 40/60*         (2018.01)
    *G07C 3/00*          (2006.01)

(56) References Cited

U.S. PATENT DOCUMENTS

| | | | |
|---|---|---|---|
| 2009/0300429 A1* | 12/2009 | McCroskey | G06F 11/0739 714/48 |
| 2017/0236064 A1 | 8/2017 | Kirschnick | |
| 2018/0144243 A1* | 5/2018 | Hsieh | G06F 30/20 |
| 2019/0086911 A1* | 3/2019 | Xin | G05B 23/0283 |

OTHER PUBLICATIONS

Kruckenberg, Fault Diagnosis and Hardware in the Loop Simulation for the EcoCAR Project, 2011, https://etd.ohiolink.edu/apexprod/rws_etd/send_file/send?accession=osu1306180272&disposition=inline (Year: 2011).*

Anonymous: "Forum "Motion & Drives"; Hannover Messe 2018—Predictive Maintenance", .Apr. 23, 2018 (Apr. 23, 2018), pp. 1-9, XP055522457; Retrieved from the Internet URL:https://bearingworld.org/fileadmin/content/News/2018/0318/Programm Forum Motion and Drives 2018.pdf; 2018.

European Search Report Application No. 18173511.9 dated Nov. 28, 2018.

\* cited by examiner

| warning message 1 | defect A | A' |
|---|---|---|
|  | defect B | B' |
|  | defect C | C' |
| warning message 2 | defect D | |
|  | defect F | |
| warning message 3 | defect E | |

METHOD FOR GENERATING A KNOWLEDGE BASE USEFUL IN IDENTIFYING AND/OR PREDICTING A MALFUNCTION OF A MEDICAL DEVICE

PRIORITY STATEMENT

The present application hereby claims priority under 35 U.S.C. § 119 to European patent application number EP18173511.9 filed May 22, 2018, the entire contents of which are hereby incorporated herein by reference.

FIELD

Embodiments of the application generally relate to a method, a computer program product and a computer readable medium for generating a knowledge base useful in identifying and/or predicting a malfunction of a medical device. Embodiments of the application also generally relate to a respective knowledge base and the use of such knowledge base in proving customer service for medical devices.

BACKGROUND

Medical devices, in particular medical imaging devices, such as magnetic resonance imaging (MRI) device or computer tomography (CT) imaging devices are well known in the state of the art. These medical devices are constructed by numerous components such as a patient table, an X-ray tube, a gantry, thus a plurality of mechanical and electrical components such as capacitors, resistors, circuitries, integrated circuits, microprocessors, memory modules and the like. These medical devices have an enormous level of complexity. Many components are purchased from suppliers, in particular from different suppliers, or are developed by different teams. For such highly complex devices, only a few experts are available that fully understand a device end to end. Additionally, device specific experience can only be gathered over time and from known devices being available.

In order to guarantee a long life of the medical device, regular maintenance is typically provided, for example, organized by a customer care centre. The main part is reactive service, where service is done after a problem was detected by the user. Further, many medical devices are adapted for remote service, i.e. service notifications are triggered by the medical device and sent to the customer care centre e.g. via a cloud. It is desirable that such service notifications are triggered in time for providing maintenance well before a malfunction affects the operation of the medical device. These triggered events depend on templates that are developed based on experience values collected for the specific type of medical device.

SUMMARY

The inventors have discovered, however, that such experience values are not available for newly developed medical device, since the needed knowledge must be gathered over time by experience. Due to high product quality and rigorous testing of medical devices, a defect probability of malfunctions occurring in the beginning of the lifetime of the medical device is drastically reduced. As a result, experience values for a specific medical device can only be gathered at a time when an overall product lifecycle of the specific type of the medical device is about to end, for example, at a time when an updated, i.e., further developed, medical device is already available.

At least one embodiment of the present invention provides a method to support an operator in charge of maintenance to identify an error or defect of a medical device, in particular, a newly developed medical device.

At least one embodiment the present invention provides an operator with a way to predict defects which are likely to affect the operation of a medical device, in particular, a newly developed medical device.

Embodiments of the application are directed to a method for generating a knowledge base useful in identifying and/or predicting a malfunction of a medical device; a computer program product; a computer readable computer medium; a knowledge base; and a use thereof.

Particularly advantageous embodiments and features of the invention are given by the claims as revealed in the following description. Features of different claim categories may be combined as appropriate to give further embodiments not described herein.

In the following, embodiments of the invention are described with respect to a processor of a workstation as well as with respect to the claimed methods. Features, advantages or alternative embodiments herein can be assigned to the other objects and vice versa. In other words, the processor of the workstation can be improved with features described or claimed in the context of the methods. In this case, the functional features of the method are embodied by objective units of the processor.

According to a first embodiment of the present invention, a method for generating a knowledge base configured to identify and/or predict a malfunction of a medical device is disclosed, wherein the medical device includes electrical and/or mechanical components as well as medical device software, wherein in operation of the medical device, the medical device software generates warning messages based on output parameters measured at the medical device, wherein the method comprises:

(a) providing virtual components, wherein each virtual component corresponds to a component of the medical device;
(b) creating a virtual model by using the virtual components, wherein the virtual model corresponds to the medical device,
(c) rendering at least one virtual output parameter of the virtual model based on simulating a malfunction of at least one virtual component,
(d) providing the at least one virtual output parameter to the medical device software, in particular determining the response of the medical device software to the at least one virtual output parameter and
(e) correlating the response of the medical device software to the at least one virtual output parameter, in particular any warning message generated by the medical device software, to the simulated malfunction of the at least one virtual component;

wherein (c) to (e) are repeated for a plurality of different simulated malfunctions, and wherein the simulated malfunctions and correlated responses of the medical device software are used in the building of a knowledge base on the medical device.

At least one embodoiment of the invention also relates to a use of a knowledge base configured to identify and/or predict a malfunction of a medical device, wherein the medical device includes electrical and/or mechanical components as well as medical device software, wherein in operation of the medical device, the medical device software generates warning messages based on output parameters measured at the medical device, wherein the knowledge base is generated by a method comprising:

(a) providing virtual components, wherein each virtual component corresponds to a component of the medical device;
(b) creating a virtual model by using the virtual components, wherein the virtual model corresponds to the medical device,
(c) rendering at least one virtual output parameter of the virtual model based on simulating a malfunction of at least one virtual component,
(d) providing the at least one virtual output parameter to the medical device software,
(e) correlating the response of the medical device software to the at least one virtual output parameter, in particular any warning message generated by the medical device software, to the simulated malfunction of the at least one virtual component;
wherein steps (c) to (e) are repeated for a plurality of different simulated malfunctions, and wherein the simulated malfunctions and correlated responses of the medical device software are used in the building of a knowledge base on the medical device.

In another embodiment of the present invention, it is provided that the knowledge base is used in designing a new version of the medical device. In particular, the knowledge base may identify design flaws at an early state of a newly designed medical device.

In another embodiment of the present invention, it is provided that the knowledge base is used in designing a new version of the medical device. In particular, the knowledge base may identify design flaws at an early state of a newly designed medical device.

Preferably, a further embodiment of the invention is a processor of a workstation, configured for performing at least one of the following:
providing virtual components, wherein each virtual component corresponds to a component of the medical device,
creating a virtual model by using the virtual components, wherein the virtual model corresponds to the medical device,
rendering a virtual output parameter of the virtual model based on simulating a malfunction of at least one virtual component,
providing the virtual output parameter to the medical device software,
correlating the response of the medical device software to the virtual output parameter, in particular, any warning message generated by the medical device software, to the simulated malfunction of the at least one virtual component;
repeating at least some of the previous steps for a plurality of different simulated malfunctions, and/or
building a knowledge base on the medical device.

A further embodiment of the invention is further directed to a knowledge base built by an embodiment of the inventive method. In particular, the invention relates to a machine learning system trained by an embodiment of the inventive method. Such machine learning system provides useful assistance to customer service centres providing maintenance service for medical devices of the type simulated in the virtual model.

A further embodiment of the invention is further directed to a method for configuring a knowledge base, preferably a machine learning system, by an embodiment of the inventive method. In an embodiment, the method, comprises:
configuring a machine learning system on a medical device, to at least one of identify and predict a malfunction of the medical device, the medical device including at least one of electrical and mechanical components and medical device software, in operation of the medical device, the configuring including
(a) providing virtual components, each virtual component of the virtual components corresponding to a component of the medical device;
(b) creating a virtual model of the medical device using the virtual components;
(c) rendering at least one virtual output parameter of the virtual model created, based upon simulation of a malfunction of at least one of the virtual components;
(d) providing the at least one virtual output parameter rendered, to the medical device software;
(e) correlating a response of the medical device software to the at least one virtual output parameter rendered;
wherein steps (c) to (e) are repeated, based upon a plurality of different simulated malfunctions, and
wherein the plurality of different simulated malfunctions and responses of the medical device software correlated are used in the configuring of the machine learning system on the medical device.

Further, the knowledge base may be used for optimizing data gathering, thus saving data bandwidth, in that the machine learning system may suggest suitable output parameters and the intervals in which these should be measured, as well as possibly the maintenance interval, thereby making maintenance and service more efficient.

A further embodiment of the present invention is a computer program product comprising program elements for carrying out the steps of the method according to an embodiment of the present invention, when the program elements are loaded into a memory of a workstation.

A further embodiment of the present invention is a computer-readable medium on which is stored a program element that can be read and executed by a workstation in order to perform steps of the method according to an embodiment of the present invention when the program elements are executed. The computer-readable medium may be a data carrier such as the cloud, a hard disc, CD-ROM, SD-card, or other digital medium. The workstation may be any form of digital calculating device, e.g. a PC, smart phone, tablet computer, cloud, workstation, or handheld device. Preferably, the workstation comprises a processor described in the following.

Thus, an embodiment of the invention also relates to the use of a knowledge base—preferably comprising or consisting of a machine learning system—for assisting a customer care centre in providing maintenance service for a medical device.

BRIEF DESCRIPTION OF THE DRAWINGS

The invention shall now be illustrated by way of a particular embodiment with reference to the attached drawings, in which.

DETAILED DESCRIPTION OF THE EXAMPLE EMBODIMENTS

Figure 1:
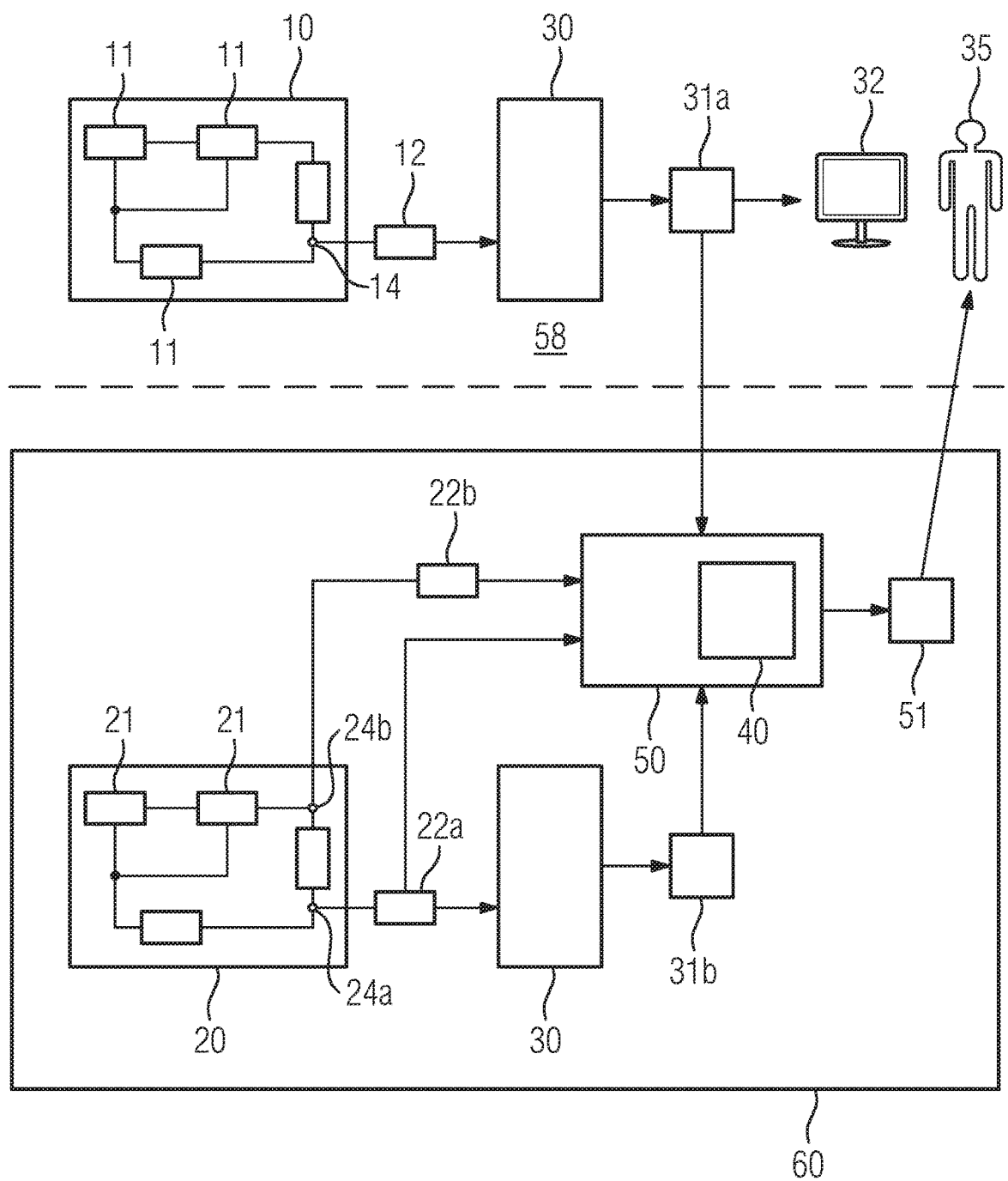
FIG. 1 schematically shows a block diagram illustrating a method for predicting a malfunction of a medical device according to a further preferred embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the following, embodiments of the invention are described with respect to a processor of a workstation as well as with respect to the claimed methods. Features, advantages or alternative embodiments herein can be assigned to the other objects and vice versa. In other words, the processor of the workstation can be improved with features described or claimed in the context of the methods. In this case, the functional features of the method are embodied by objective units of the processor.

According to a first embodiment of the present invention, a method for generating a knowledge base configured to identify and/or predict a malfunction of a medical device is disclosed, wherein the medical device includes electrical and/or mechanical components as well as medical device software, wherein in operation of the medical device, the medical device software generates warning messages based on output parameters measured at the medical device, wherein the method comprises:

(a) providing virtual components, wherein each virtual component corresponds to a component of the medical device;

(b) creating a virtual model by using the virtual components, wherein the virtual model corresponds to the medical device, (c) rendering at least one virtual output parameter of the virtual model based on simulating a malfunction of at least one virtual component, (d) providing the at least one virtual output parameter to the medical device software, in particular determining the response of the medical device software to the at least one virtual output parameter and (e) correlating the response of the medical device software to the at least one virtual output parameter, in particular any warning message generated by the medical device software, to the simulated malfunction of the at least one virtual component;

wherein (c) to (e) are repeated for a plurality of different simulated malfunctions, and wherein the simulated malfunctions and correlated responses of the medical device software are used in the building of a knowledge base on the medical device.

Contrary to the state of the art, a knowledge base that correlates warning messages to malfunctions and defects is formed according to the present invention, wherein the experience of the knowledge base is the result of a simulation. By repeating the steps (c) to (e), the knowledge base gathers experience on the medical device by simulating malfunctions or defects of individual or several components, instead of gathering the experience over the lifetime of the real medical device. As a result, it is advantageously possible to already provide the knowledge base at the beginning of the lifetime of the medical device. In particular, the operator in charge of maintenance may be supported by identifying a possible malfunction based on the warning message, since the knowledge base gives him an idea about the potential defect that might be correlated to the warning message.

For example, several potential malfunctions or defects might cause the same warning message and the knowledge base advantageously provides an idea which potential defect might be most likely, in particular in the context of another warning message or the age of the medical device. At least one embodiment of the invention also takes into account that the medical device software is typically not often modified, and thus, the medical device software cannot be easily updated to reflect newly identified correlations between defects and output parameters. As a consequence, the operator depends on the response of the medical device software, in particular the content of the warning message. By using at least one embodiment of the invention, it is advantageously possible to rely on the knowledge base for identifying or isolating the defect from the warning message, in particular in such cases when the correlation between the defect and the output parameter is ambiguous.

The "knowledge base" may comprise a collection of numerous simulated malfunctions and the related responses of the medical device software, in particular the content of the corresponding warning message, or the fact that no warning message was issued. In its simplest form, the knowledge base is a database including e.g. a list of simulated malfunction and the related simulated responses of the medical device software. In this case, the "correlation" is the recording in the knowledge base that a certain response of the medical device software occurred as a result of a particular malfunction.

In other embodiments, the correlation between the warning message and the defect takes into account further information, for example one or several virtual output parameters which were "measured" during the simulation of gathered in the simulation of a malfunction. In useful embodiments, the knowledge base is trained to consider several aspects, such as the age of the medical device and other previous warning messages, for correlating one or more defects to one specific warning message. In other words, the knowledge base replaces the long-term experience of the operator, e.g. an human customer service employee, that could identify a defect from a general warning message by using his experience over the previous lifetime of the medical device.

Thus, at least one embodiment of the invention is particularly useful in providing maintenance service to newly developed medical devices, where long-term experience is not available. Preferably, the knowledge base provides a probability for a specific malfunction or defect and/or a list of different potential malfunctions together with a respective probability value. In particular, the knowledge base comprises a table of correlations and/or a machine learning algorithm which is trained based on correlations.

In preferred embodiments, the term "output parameters" represents measurable parameters that can be detected at the real medical image device during its operation. For example, the output parameter is a voltage of a specific capacitor or the like. The output parameter might be a frequency and/or an amplitude of a signal. The signals might be digital or complex, such as error messages and/or error codes of the individual component. In general, a deviation of the output parameter originates from a defect associated with the component providing the output parameter and/or a different component that is in relationship with the component providing the output parameter and that causes the deviation from the default output parameter due to its defect.

For example, the capacitor has a defect, and/or a resistor connected to the capacitor has a defect. Both defects might lead to deviation from the output parameter. Further, the "virtual output parameter" corresponds to the "output parameter" that is measured in operation, but it is the result of simulation. As a consequence, it is possible to replace the medical device and its output parameter measured over time by the virtual model including its simulated virtual output parameters.

The term "warning message" is used in this application for any kind of notification, in particular, in form of a transferred and displayed information that is provided to the operator, and includes information on the status of the medical device. The warning message is generated by the medical device software as a response to a measured output parameter and e.g. displayed on a screen, or may be transferred to a customer care centre as part of a remote service system, e.g. via a cloud or over the internet, especially automatically. Thus, in useful embodiments the medical device software controls and/or monitors the functions of the medical device.

The warning message is forwarded or sent to a server, in particular to a central managing server, that, for example, coordinates the maintenance, and the message is then displayed on a screen. Preferably, the knowledge base is located at the server. For example, the warning message is displayed to the operator on a screen of the medical device directly after an abnormality of the output parameter is identified. Thus, the operator can adjust the further maintenance strategy in real time.

In particular, the warning message includes information that a difference between a standard value and an actual output parameter exceeds a threshold value. For example, the warning message states "the voltage at the capacitor B at the motherboard dropped to a value of 0.5 $\mu V$". In this embodiment, the warning message does not inform the operator about a failure or defect of a component, but rather, it provides information about a deviation of a specific or several different specific output parameters from the corresponding default value. Such warning messages are evidently most useful in providing maintenance service, since they allow providing service, e.g. replacing defective components, before complete failure and resulting downtime of the medical device.

The term "virtual model" means that a design of the medical device, in particular an arrangement and/or connection of the components is simulated. In particular, the "virtual model" is formed from virtual components that correspond to the real components of the medical device. For example, a visual programming software, such as Agilent VEE or Labview, is used for creating a virtual model of the medical imaging device. In such visual programming software tools, each virtual component can be incorporated and connected with each other in a way comparable to a circuit diagram. In particular, the virtual model takes into account the effect or influence of each component individually and/or the effects arising from the interaction between components.

For example, it might be known that a defect in a first component causes a specific defect in a second component being connected to the first component. The simulation might consider this effect even though this defect has no influence on the output of the second component, as it might influence the functionality of a third component being connected to the second component. It is also conceivable that the third component is connected to the first and the second components.

Preferably, the simulation then differs between an effect on the third component depending on a malfunction of the first component, a malfunction of the second component, and a malfunction of the first and the second components, wherein the effect on the malfunction of the first and the second components differs from the addition of the effects caused by the malfunctions of the first component and the second component individually. In particular, the effects assigned to the respective component or arising from the interaction of components is included in the simulation of the malfunction of the respective component.

In an embodiment, the virtual model is set up by an operator, for example, by using a human machine interface such as keyboard, a mouse, a touchpad, or the like. In other embodiment, the virtual model is generated from the digital construction plans used in the construction of the particular type of medical device, in particular the CAD (Computer Aided Design) Files. Such CAD Files contain in particular the electrical layout of the type of medical device, but also the or part of the mechanical construction. In particular, the virtual model may be a "digital twin" of the medical device.

Usually, the virtual model will be modelling a particular type of medical device, which is manufactured and sold in many individual specimens. The virtual models simulates all following impacts caused by the failure or malfunction of one or several components. These impacts might lead to an abnormality of one or several output parameters. For example, a main capacitor is failing on the detector circuit board, which leads to a drop in voltage, and so on. Finally, this leads to a malfunction of a certain device. In other words, the simulation models every voltage and every consequent event and renders the output data to feed the actual medical device software.

Preferably, the term "medical device", when used in the context of the generation of the knowledge base, describes a particular type of medical device, in particular of medical imaging device, such as a type of a nuclear medicine (NM) scanner, a positron emission tomography (PET) scanner, an X-ray scanner (XA), fluoroscopy (RF) scanner, or mammography (MG) scanner. For example, the type of the medical device is categorized by its version or generation. However, the knowledge base is preferably used in assisting in the maintenance of one or several individual medical devices of that particular type, in particular of individual medical devices installed at medical centres, and for which (e.g. remote) customer service is provided. For example, the risk for the malfunction is provided for an individual medical device.

Particularly advantageous embodiments and features of the invention are given by the claims as revealed in the following description. Features of different claim categories may be combined as appropriate to give further embodiments not described herein.

At least one embodiment of the invention also relates to a use of a knowledge base configured to identify and/or predict a malfunction of a medical device, wherein the medical device includes electrical and/or mechanical components as well as medical device software, wherein in operation of the medical device, the medical device software generates warning messages based on output parameters measured at the medical device, wherein the knowledge base is generated by a method comprising:
(a) providing virtual components, wherein each virtual component corresponds to a component of the medical device;
(b) creating a virtual model by using the virtual components, wherein the virtual model corresponds to the medical device,
(c) rendering at least one virtual output parameter of the virtual model based on simulating a malfunction of at least one virtual component,
(d) providing the at least one virtual output parameter to the medical device software,
(e) correlating the response of the medical device software to the at least one virtual output parameter, in particular any warning message generated by the medical device software, to the simulated malfunction of the at least one virtual component;
wherein steps (c) to (e) are repeated for a plurality of different simulated malfunctions, and wherein the simulated malfunctions and correlated responses of the medical device software are used in the building of a knowledge base on the medical device.

According to a useful embodiment, during operation of an individual medical device, i.e., after the knowledge base has been built, a warning message generated by the medical device software may be fed to the knowledge base, and a probability value is provided by the knowledge base, wherein the probability value specifies a probability for a malfunction of a certain component. Consequently, the operator is informed about the probability that the warning message is caused by a specific defect. Thus, it is, for example, possible for the operator to evaluate whether maintenance is needed immediately or whether repairing the malfunction of the identified component at the next regular maintenance is sufficient.

In particular, a list of probabilities may be provided, wherein the list respectively ranks the probability for a specific defect. For example, the list caused by a warning is read as follows: "The probability that defect A caused the warning message is a %, the probability that defect B caused the warning message is b %." Thus, several potential defects as well as the corresponding probabilities are provided to the operator. Such probability values may be generated by the knowledge base by the use of statistical evaluations on the simulated malfunctions, i.e. by analysing the malfunctions, which caused a specific warning message, and assigning probability values accordingly. In a further useful embodiment, the knowledge based includes a machine learning system using e.g. deep learning algorithms, and which accordingly is trained by the simulated malfunctions to recognise a certain malfunction from the warning message.

According to a useful embodiment, it is provided that the probability value is adapted by the knowledge base when a subsequent warning message is generated by the medical device software. For example, the knowledge base has the information that the combination of two different warning messages within a certain time interval indicates a specific defect of a certain component or at least increases the probability that the defect has occurred. Thus, it is possible to extract further information from a sequence of warning messages. For example, the list mentioned above is read as follows: "The probability that defect A occurred has changed from a % to a'%; The probability that defect B occurred has changed from b % to b'%."

Preferably, it is provided that a sequence of malfunctions is simulated by the virtual model for producing a sequence of virtual output parameters and corresponding warning messages. Thus, it is advantageously possible to correlate a warning message sequence to a malfunction sequence that might originate from an individual failure of one component that causes further defects in other components. As a consequence, the warning messages following the first warning message can be used for isolating the defect component. Further, it is conceivable that a time development, i.e., the time interval between two warning messages, may also be used for identifying the defect component or components. In particular, the term "sequence" means that several warning messages are produced one after the other.

In particular, the period between two warning messages and/or the type of warning message that follow each other might be used for identifying or predicting a malfunction. For example, a first warning message states, "The voltage of condensator B has been dropped". A second message is subsequently generated and states, "The voltage of condensator C has been dropped". The sequence of these two warning messages might indicate a certain defect or malfunction of the medical imaging device that even might be different from the defect that might be reasonable after receiving the first warning message. Preferably, a time interval between the first warning message and the second warning massage is also considered for ruling out a potential defect or for predicting a malfunction.

In particular, it is provided that a time evolution of the virtual component is taken into account in the simulation. That means that an aging of the virtual component is taken into account. For example, the probability that a component reacts in a certain way depends on its age. The aging of the components might be known and is incorporated into the simulation such that a reaction of the virtual components to a defect of another virtual component also depends on the simulated age of the virtual component. Thus, it advantageously possible to take the aging of each component into account. This means that the knowledge base can use the timing of the warning message, i.e., the time interval starting from the installation of the particular medical device until the event of the warning message, for identifying the probability that a specific defect is correlated to the warning message being provided in operation of the real medical imaging device.

According to a preferred embodiment of the invention, it is provided that the knowledge base includes a machine learning system, preferably by a deep learning system. In some embodiments, the knowledge base is a machine learning system.

In particular, the machine learning system is trained by the input to the knowledge base, such as warning messages and the simulated malfunctions, and optionally the simulated virtual output parameters. By using a machine learning system, it is advantageously possible to identify general concepts and/or correlations that are not obvious when simply listing the collected data in a database.

In particular, the machine learning system uses an artificial network, for example, realized at a server. Moreover, the machine learning system might correlate warning messages that do not seem to be correlated with each other at the first glance. In particular, it is provided that the trained artificial network has an input layer, a plurality of hidden layers and an output layer. For example, the output parameter and/or the warning message is provided to the input layer, and preferably, each potential output parameter and/or each potential warning message is assigned to a node of the input layer. It is also possible that sequences of warning messages are used as input parameters, then advantageously sequences of potential output parameters and/or potential warning messages are assigned to a node of the input layer, furthermore, it is possible to use the time difference between the measurement of the potential output parameters and/or the time difference between the potential warning messages as input parameters, in particular to assign them to a node of the input layer.

In particular, the nodes of the input layer can correspond to two-dimensional inputs, wherein a first dimension corresponds to potential output parameters and/or potential warning messages, and wherein a second dimension corresponds to a time interval. The output layer then provides a probability that a certain component has a defect. Each node of the output layer is assigned to a certain component and outputs the corresponding probability for a defect of the certain component. In order to train the artificial network, the virtual output parameters as well as information about the corresponding defect are provided to the artificial network. In particular, the virtual output parameters are provided to the nodes of the input layer. Further, the artificial network is trained by a sequence of virtual output parameters generated by the virtual model. Thus, the knowledge base gathers experience based on virtual output parameters and preferably by its order.

Considering that simulating malfunctions for each component and/or serval components results in a huge amount of data, the machine learning system helps to handle this large amount in order to extract information that can be used in the knowledge base of this type of medical device. The machine learning system transforms the knowledge base from a knowledge base that only correlates defects and warning messages to an experienced knowledge base. Another advantage is that the machine learning system realizes correlations and interrelationships such that there is no need to repeat the whole simulation after a small hardware change at the medical device or in the case of a small software change regarding the medical device software. Further, the machine learning system can be trained not only by the (simulated) warning messages which would be visible to the operator, but also by the virtual output parameters provided by the virtual model, which are usually fed to the medical device software. Since the machine learning system can process more information, it may thus also be provided with such deep system information of the medical device.

In a useful embodiment, the machine learning system is trained by at least one further virtual output parameter simulated using the virtual model, the further virtual output parameter not corresponding to an output parameter measured at the medical device in operation. Since the machine learning system is learning not from a real medical device, but from a virtual model thereof, it is not restricted to processing the output parameters (e.g. voltages, currents . . . ) which are actually available, i.e. which are actually measured, at such a medical device in real life. Rather, the virtual model may provide all sorts of output parameters; it may "measure" the voltage or current at points where in reality no such sensor is available. This will improve the accuracy of any predictions made by the machine learning system.

In another embodiment, it is provided that a new output parameter is identified and provided by the machine learning system, wherein the new output parameter is measured in a different way than the output parameters measured at the medical device in operation. Thus, the machine learning system may determine optimized measuring points within the medical device. For example, the machine learning system suggests measuring another output parameter, such as a voltage at a different capacitor, since measuring the new output parameter provides an improved reliability for identifying a specific defect or being correlated to a bigger number of components. It is also conceivable that the machine learning system suggests measuring a new output parameter as response to a specific warning message. For example, the machine learning system identifies two potential defects correlated to one warning message, and the machine learning system further realizes that measuring another new output parameter can exclude or confirm one of these potential defects. Thus, the machine learning system might suggest measuring the new output parameter. It is even conceivable that the knowledge base informs the operator of measuring the new output parameter after said warning message was generated, in order to accelerate the identification of the defect.

Furthermore, it is preferably provided that a new maintenance interval is identified and provided by the machine learning system, wherein the new maintenance interval differs from the previous maintenance interval. For example, the machine learning system suggests to change the maintenance interval when one or several warning messages indicate a failure of a component or sub-unit of the medical device in the near future. Thereby, optimized sampling cycles within the medical device useful for predictive maintenance may be determined.

For providing a new output parameter and/or a new maintenance model, the virtual model is simulated for different output parameters and/or different sequences of warning messages. As a consequence, it is possible to provide the simulated output parameter to the artificial network, in particular to certain nodes in the input layer, and check whether the probability for a certain defect can be deduced from the new output parameter. For example, the new output parameter reduces the number of potential defects compared to the previous output parameter. It is also conceivable that the trained virtual artificial network predicts a crucial defect of one component depending on the warning message of a sequence of warning messages in the near future. By adapting the maintenance timing, it is possible to react in time.

In another embodiment, it is provided that the measured output parameter is an output of a sensor, in particular a current, a voltage. The sensor may also be used to observe the status of a mechanical component. For example, the sensor detects an oscillation of a magnet used by a magnetic imaging device. The change of the frequency might a result of defect at the magnet, for instance. Further, it is conceivable that the output parameters are observed continuously or from time to time. In particular, it is provided that a deviation of the measured parameter from a default value triggers the generation of the warning message. Further components might be a patient table, an X-ray tube, a capacitor, resistors, circuitries, integrated circuits, microprocessors, memory modules, and the like.

In another embodiment of the present invention, it is provided that the knowledge base is used in designing a new version of the medical device. In particular, the knowledge base may identify design flaws at an early state of a newly designed medical device.

Further, the knowledge base may be used for optimizing data gathering, thus saving data bandwidth, in that the machine learning system may suggest suitable output parameters and the intervals in which these should be measured, as well as possibly the maintenance interval, thereby making maintenance and service more efficient.

A further embodiment of the present invention is a computer program product comprising program elements for carrying out the steps of the method according to an embodiment of the present invention, when the program elements are loaded into a memory of a workstation.

A further embodiment of the present invention is a computer-readable medium on which is stored a program element that can be read and executed by a workstation in order to perform steps of the method according to an embodiment of the present invention when the program elements are executed. The computer-readable medium may be a data carrier such as the cloud, a hard disc, CD-ROM, SD-card, or other digital medium. The workstation may be any form of digital calculating device, e.g. a PC, smart phone, tablet computer, cloud, workstation, or handheld device. Preferably, the workstation comprises a processor described in the following.

Preferably, a further embodiment of the invention is a processor of a workstation, configured for performing at least one of the following:
 providing virtual components, wherein each virtual component corresponds to a component of the medical device,
 creating a virtual model by using the virtual components, wherein the virtual model corresponds to the medical device,
 rendering a virtual output parameter of the virtual model based on simulating a malfunction of at least one virtual component,
 providing the virtual output parameter to the medical device software,
 correlating the response of the medical device software to the virtual output parameter, in particular, any warning message generated by the medical device software, to the simulated malfunction of the at least one virtual component;
 repeating at least some of the previous steps for a plurality of different simulated malfunctions, and/or
 building a knowledge base on the medical device.

The term "workstation" preferably refers to a (personal) computer, a virtual machine running on host hardware, a microcontroller, or an integrated circuit. As an alternative, the workstation can be a real or a virtual group of computers (the technical term for a real group of computers is "cluster", the technical term for a virtual group of computers is "cloud"). Preferably, the workstation comprises a calculation unit, a processor, interfaces and/or a memory unit. A calculation unit can comprise hardware elements and software elements, for example, a microprocessor or a field programmable gate array. A memory unit can be embodied as a non-permanent main memory (e.g. random access memory) or as a permanent mass storage (e.g. hard disk, USB stick, SD card, solid state disk). The workstation can be part of the medical device.

A further embodiment of the invention is further directed to a knowledge base built by an embodiment of the inventive method. In particular, the invention relates to a machine learning system trained by an embodiment of the inventive method. Such machine learning system provides useful assistance to customer service centres providing maintenance service for medical devices of the type simulated in the virtual model.

Thus, an embodiment of the invention also relates to the use of a knowledge base—preferably comprising or consisting of a machine learning system—for assisting a customer care centre in providing maintenance service for a medical device.

Wherever not already described explicitly, individual embodiments or their individual aspects and features can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

In FIG. 1, a block diagram illustrating a method for identifying a potential defect of a medical device 10 is schematically shown. The upper part 58 of FIG. 1 illustrates an individual medical device 10, and related actions taking place in the operation of such device, whereas the lower part 61 of FIG. 1 illustrates the virtual model and related method steps.

The medical device 10 might be a medical imaging device a magnetic resonance imaging device or computer tomography device. These devices 10 are formed by a plurality of components 11, preferably mechanical and electrical components 11. Each of the components 11 might be a source for an error that could lead to a malfunction of the medical device. For reducing the probability of failure, maintenance procedures are performed on a regular basis. For example, the maintenance procedures are triggered by a medical device software 30 that, during operation of the medical device 10, generates warning messages 31*a* based on output parameters 12, such as a voltage of an electrical component, measured at the medical device 10 by a sensor 14. The measured output parameter 12 is used as input for the medical device software 30 in order to identify an abnormality and/or a defect of the medical device 10. For doing so, the medical device 10 comprises an analysis unit for performing a medical device software 30.

For example, those warning messages are transferred to a cloud, network or server, in particular a service management system, in order to inform an operator 35 about an abnormality detected at the medical device 10. It is also conceivable that the medical device software 30 is located at the server and the output parameters 12 are transferred to the server. In particular, the medical device software 30 initiates or triggers communication of the warning message 31 when a significant modification of the output parameter 12 is identified. It is also conceivable that the output parameter 12 specifies a status of a mechanical component 11, for example, the orientation of the table, by using a corresponding sensor 14. The warning message 31*a* may be displayed to an operator 35 at a screen 32, whether directly by the medical device 10, or at a service centre.

In general, the warning message 31 informs the operator 35 about a specific status of the output parameter 12. For example, the warning message 31*a* says, "the voltage of the capacitor dropped to a critical level." However, the reason for the specific status can be manifold. For example, the drop of the voltage is caused by a defect of a resistor or, alternatively, by a defect of another component 11. As a consequence, the operator in charge of the maintenance is not able to unambiguously assign the defect or problem to the content of the warning message 31. However, an experienced expert of such a device 10 might be able to identify or correlate the defect due to his experience based on the content of the warning message.

Due to the quality of the components 11, the risk or probability for an error or a defect is quite low, in particular at the beginning of the lifetime of the respective medical device 10. As a consequence, there are few experience values that can be used for identifying the kind of a defect or potential defect based on the warning message 31 provided by the medical device software 30. It is even possible that defects or errors occur when the next generation of medical devices 10 is already available. Thus, the information about these defects cannot be used for the new generation of medical device 10 as experience values.

For optimizing a lifetime of the medical device 10 and for supporting the operator by identifying errors, it is provided to create or adapt a virtual model 20 of the medical device 10, in particular of the individual medical device 10. Preferably, a workstation 60 comprising a processor which is configured for creating and providing the virtual model 20 of the medical device 10. Thereby, the processor is preferably included in a workstation, a (personal) computer, sever and/or cloud computer. For example, the virtual model is individually set up for the specific medical device 10 by the operator. Thereby, the virtual model 20 corresponds to the medical device 10. In particular, the virtual model 20 is formed by virtual components 21 that correspond to the real components 11 of the medical device. Thereby, the virtual model 20 takes into account the effect of the respective component 11 and its interaction with other components 11.

It is also thinkable that a construction plan of the medical device 10, for example, in the form of a CAD file, is provided to the processor, each component 11 is identified, and a virtual model 20 is constructed. For example, the construction plan is scanned and the processor constructs the virtual model 20 automatically based on the information extracted from the scanned construction plan.

For identifying potential errors and malfunctions it is provided that virtual output parameters 22*a*, 22*b*, which correspond to virtual measurements taken at points 24 and 24*b*, respectively, are rendered by simulating malfunctions or defects of the virtual components 21, in particular of each virtual component 21 and each combination of malfunctions of these virtual components 21. The resulting virtual output parameters 22*a* are provided to a copy of the medical device software 30 which is e.g. installed on the processor or network. As a consequence, it is possible to correlate the response of the medical device software 30 to the simulated malfunction. By repeating this for a plurality of different simulated malfunctions, it is advantageously possible to build up a knowledge base 50. In other words, for gathering experience regarding the response of the medical device software 30 to potential output parameters 12 the medical device 10 is replaced by the virtual model 20, in particular by the virtual output parameters 22, simulated for the individual medical device 10.

In the virtual model 20, it is possible not only to gather the virtual output parameter 22*a*, measured at a point 24*a* corresponding to a sensor 14 in the medical device 10. Rather, one may gather additional virtual output parameters, such as output parameter 22*b* taken from a point 24*b* which has no corresponding sensor in the actual medical device 10. Such virtual output parameters 22*b* are nonetheless useful in gathering deep knowledge on the medical device 10, and are thus provided to the knowledge base 50. Further, the knowledge base 50 may find that such additional virtual output parameters 22*b* are more useful in providing information on present or future defects of the medical device, and thus may suggest that measurements should be taken at points 24*b* rather than 24*a*, and thus may provide useful input in designing future types of the medical device.

Preferably, a machine learning system 40, such as a deep learning system is used as part of the knowledge base 50, in particular for identifying correlations between the simulated malfunctions/defects and the warning message 31*b*. Such a machine learning system 40 is preferably integrated in the network or server and is trained by the (simulated) warning messages 31*b* and the simulated defects, and optionally also by the corresponding virtual output parameters 22*a* and 22*b*.

As a consequence, the network including the machine learning system becomes an expert on the individual medical device 10. For example, the machine learning system 40 identifies a defect based on a sequence of warning messages 31*a* generated from an individual medical device 10, and/or the trained knowledge base 50 provides a probability that a specific defect has occurred or a further defect will occur depending on the warning message 31*a*. Furthermore, the machine learning system 40 might provide a probability 51 that a total failure occurs within a defined time interval to the operator 35 of the medical device 10. Thus, it is possible to organize the maintenance effectively.

It is also conceivable that the machine learning system 40 is configured for identifying output parameters that are more suitable for isolating/identifying a defect than those output parameters 12 that are measured by default or in the past. By changing the output parameters 12, the medical device software might be adapted correspondingly. It is also conceivable that the machine learning system 40 determines a timing for measuring the output parameter 12. As a consequence, sampling of output parameters 12 can be optimized such that the amount of warning messages 31*a* that are transferred to the network/server is reduced, and the quality of reasonable information included in the warning message 31a is increased.

Figure 2:
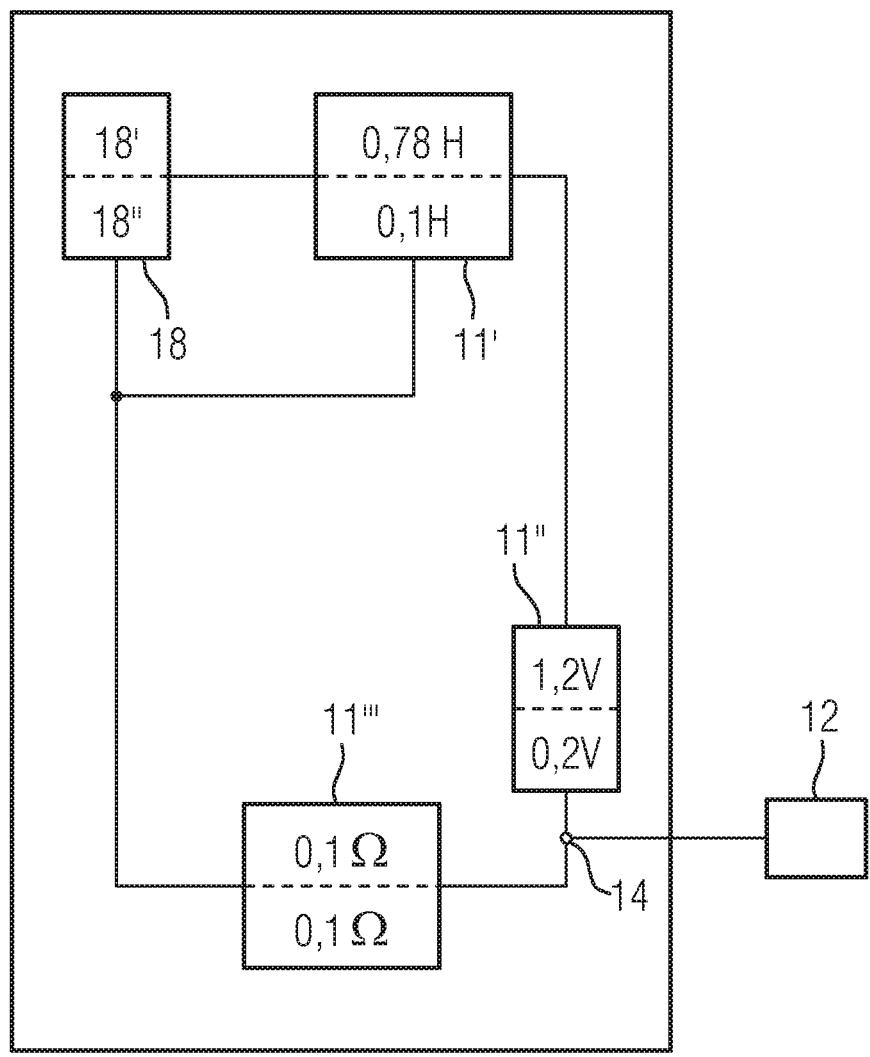
FIG. 2 schematically shows an example for a simulation using the virtual model of FIG. 1.

In FIG. 2, an example for a simulation using the virtual model 20 of FIG. 1 is illustrated. Within this example, the medical device 10 comprises a driver element 18, such as a gate driver, as well as a first component 11', a second component 11" and a third component 11'". For simulating a malfunction in the corresponding virtual model 20, it is assumed that the driver element 18 has a specific defect, such as short circuit of a capacity. As a result, a defect output 18" of the virtual element corresponding to the driver element 18 differs from a normal output 18' that is usually output by the driver element 18. However, the defective output 18" causes a drop of an inductivity at the virtual element corresponding to the first component 11', for example, from 0.78 pH to 0.1 pH, and a drop of a voltage at the virtual element corresponding to the second component 11", for example, from 1.2 V to 0.2 V (in FIG. 2 at the top of each component respectively: values expected for the normal output 18'; at the bottom: values expected for the defective output 18").

The described change of the simulation of the parameters can be determined by simulating the malfunction within the virtual model 20. It is also conceivable that the defective output 18" has no effect on a component, such as the virtual element corresponding to the third component 11'", which also can be determined by simulating the malfunction within the virtual model 20. In the illustrated simulation the resistance maintains $0.1\Omega$. However, the defective output 18" at the virtual element corresponding to the driver element 18 has an effect on the virtual output parameter 22a measured at point 24. Thus, by simulating the malfunction in the virtual model 20, it is possible to generate the virtual output parameter 22a, such as a output voltage, that is caused by a certain defective output 18" caused by a certain component, such as a driver element 18.

Figures 3, 4:
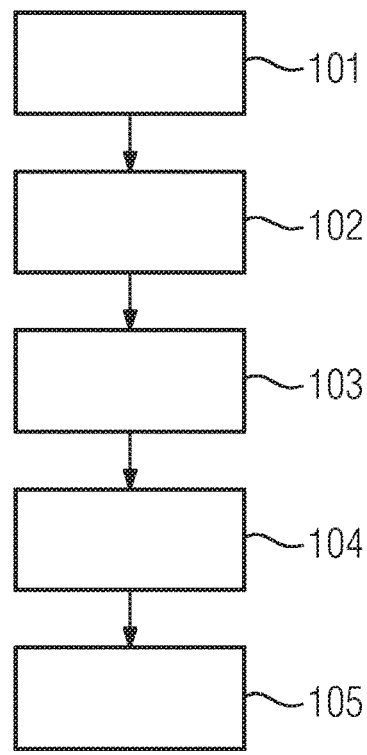
FIG. 3 schematically shows an example for a knowledge base.
FIG. 4 schematically shows a flow chart illustrating a method for predicting a malfunction of a medical device according to a further preferred embodiment.

In FIG. 3, an example of a knowledge base 50 is illustrated. For example the knowledge base 50 assigns three different defects, namely defect A, defect B and defect C, to the warning message 1. Further, the knowledge base 50 specifies the corresponding probability of the individual defect. The probability specifies the probability that the warning message has been caused by the corresponding defect. For example, the knowledge base 50 correlates the probability A' to defect A, the probability B' to defect B and the probability C' to defect C, wherein the probability A' is the probability that the warning message 1 has been caused by defect A, wherein the probability B' is the probability that the warning message 1 has been caused by defect B, and wherein the probability C' is the probability that the warning message 1 has been caused by defect C. It is also conceivable that the knowledge base 50 only identifies typical defects, such as the defect D and the defect F for warning message 2 without specifying the probability. In some cases, a warning message 3 might be even correlated to only one potential defect. In particular, a defect can specify one component or several components being defect, furthermore.

In FIG. 4, a flow chart illustrating a method for predicting a malfunction of a medical device according to a further preferred embodiment is shown. In particular, the method comprises
(a) providing 101 virtual components, wherein each virtual component corresponds to a component of the medical device;
(b) creating 102 a virtual model 20 of the medical device 10 by using the virtual components 21;
(c) rendering 103 at least one virtual output parameter 22 of the virtual model 20 based on simulating a malfunction of at least one virtual component 21,
(d) providing 104 the at least one virtual output parameter 22 to the medical device software;
(e) correlating 105 the response of the medical device software 30 to the at least one virtual output parameter 22, in particular any warning message 31 generated by the medical device software, to the simulated malfunction of the at least one virtual component 21;
Repeating (f) steps (c) to (e) for a plurality of different simulated malfunctions and
feeding a warning message generated by the medical device software 30 to the knowledge base 50, and in response the knowledge base 50 provides a probability value 51, wherein the probability value 51 specifies a probability for a malfunction of a certain component 11.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:
1. A method for generating a knowledge base configured to at least one of identify and predict a malfunction of a medical device, the medical device including at least one of electrical and mechanical components and medical device software, in operation of the medical device, the method comprising:
(a) providing virtual components, each virtual component of the virtual components corresponding to a component of the medical device;
(b) creating a virtual model of the medical device using the virtual components;

(c) rendering at least one virtual output parameter of the virtual model created, based upon simulation of a malfunction of at least one of the virtual components;

(d) providing the at least one virtual output parameter rendered, to the medical device software;

(e) correlating a response of the medical device software to the at least one virtual output parameter rendered;

wherein steps (c) to (e) are repeated, based upon a plurality of different simulated malfunctions, and wherein the plurality of different simulated malfunctions and responses of the medical device software correlated are used in the generating of the knowledge base on the medical device.

2. The method of claim 1, wherein a sequence of malfunctions is simulated by the virtual model.

3. The method of claim 1, wherein a time evolution of a virtual component of the virtual components, is taken into account in simulating the malfunction of the virtual component.

4. The method of claim 2, wherein the knowledge base includes a machine learning system.

5. The method of claim 4, further comprising:
training the machine learning system based on the malfunctions simulated and correlated responses of the medical device software.

6. The method of claim 4, wherein the machine learning system is trained by at least one further virtual output parameter simulated using the virtual model.

7. The method of claim 4, wherein a new output parameter is identified and provided by the machine learning system.

8. The method of claim 4, wherein a new maintenance interval is identified and provided by the machine learning system, wherein the new maintenance interval differs from a previous maintenance interval.

9. The method of claim 7, wherein the new output parameter identified is at least one of a current, a voltage and an output of a sensor.

10. A non-transitory computer program product storing program code instructions for carrying out the method of claim 1 upon the program code instructions being loaded into a memory of a workstation and upon the program code instructions being executed on the workstation.

11. A non-transitory computer-readable medium storing program code instructions, readable and executable by a workstation, to perform the method of claim 1 upon the program code instructions being executed by the workstation.

12. The method of claim 1, wherein the medical device software is configured to generate warning messages based on virtual output parameters measured at the medical device and wherein step (e) includes
(e) correlating a warning message of the warning messages, generated by the medical device software, to the malfunction of the at least one virtual component simulated.

13. The method of claim 12, wherein a sequence of malfunctions is simulated by the virtual model for producing a sequence of virtual output parameters and corresponding warning messages.

14. The method of claim 12, wherein a time evolution of a virtual component of the virtual components, is taken into account in simulating the malfunction of the virtual component.

15. The method of claim 13, wherein a time evolution of a virtual component of the virtual components, is taken into account in simulating the malfunction of the virtual component.

16. The method of claim 4, wherein the machine learning system is a deep learning system.

17. The method of claim 13, wherein the knowledge base includes a machine learning system, and wherein the method further comprises:
training the machine learning system based on the malfunctions simulated and correlated responses of the medical device software including the warning messages.

18. The method of claim 17, wherein the machine learning system is trained by at least one further virtual output parameter simulated using the virtual model, the at least one further virtual output parameter not corresponding to an output parameter measured at the medical device in operation.

19. The method of claim 18, wherein a new output parameter is identified and provided by the machine learning system, the new output parameter being measured in a different way than the output parameters measured at the medical device in operation.

20. The method of claim 19, wherein the new output parameter measured is at least one of a current, a voltage and an output of a sensor.

21. A non-transitory computer program product storing program code instructions for carrying out the method of claim 12 upon the program code instructions being loaded into a memory of a workstation and upon the program code instructions being executed on the workstation.

22. A non-transitory computer-readable medium storing program code instructions, readable and executable by a workstation, to perform the method of claim 12 upon the program code instructions being executed by the workstation.

23. A method, comprising:
configuring a machine learning system on a medical device, to at least one of identify and predict a malfunction of the medical device, the medical device including at least one of electrical and mechanical components and medical device software, in operation of the medical device, the configuring including
(a) providing virtual components, each virtual component of the virtual components corresponding to a component of the medical device;
(b) creating a virtual model of the medical device using the virtual components;
(c) rendering at least one virtual output parameter of the virtual model created, based upon simulation of a malfunction of at least one of the virtual components;
(d) providing the at least one virtual output parameter rendered, to the medical device software;
(e) correlating a response of the medical device software to the at least one virtual output parameter rendered;
wherein steps (c) to (e) are repeated, based upon a plurality of different simulated malfunctions, and
wherein the plurality of different simulated malfunctions and responses of the medical device software correlated are used in the configuring of the machine learning system on the medical device.

24. A method, comprising:
using the machine learning system configured by the method of claim 12 in assisting a customer care centre in providing maintenance service for a medical device.

25. The method of claim 13, further comprising:
feeding, wherein in operation of the medical device, a warning message generated by the medical device software to the machine learning system; and
providing, via the machine learning system, a probability value, the probability value specifying a probability for a malfunction of a certain component.

26. The method of claim 25, wherein the probability value is adapted by the machine learning system, upon a subsequent warning message being generated by the medical device software.

27. The method of claim 25, wherein the probability value is adapted by the machine learning system, upon a subsequent warning message being generated by the medical device software.

* * * * *